(12) United States Patent
Rathinavelu et al.

(10) Patent No.: US 6,280,965 B1
(45) Date of Patent: Aug. 28, 2001

(54) SIMPLE NON-RADIOACTIVE ASSAY FOR ESTIMATING PROTEIN KINASE C AND PROTEIN PHOSPHATASE-1

(75) Inventors: Appu Rathinavelu; Andres Malave, both of Fort Lauderdale, FL (US)

(73) Assignee: Nova Southeastern University, Fort Lauderdale, FL (US)

( * ) Notice: Subject to any disclaimer, the term of this patent is extended or adjusted under 35 U.S.C. 154(b) by 0 days.

(21) Appl. No.: 09/321,253

(22) Filed: May 26, 1999

(51) Int. Cl.[7] .................................................... C12Q 1/58
(52) U.S. Cl. .............................. 435/15; 435/7.4; 435/21
(58) Field of Search .................. 435/7.4, 15, 21

(56) References Cited

U.S. PATENT DOCUMENTS

| | | |
|---|---|---|
| 4,087,331 | 5/1978 | Bucolo et al. ..................... 435/15 |
| 4,923,802 | 5/1990 | Gallis ................................ 435/15 |
| 5,141,852 | 8/1992 | Egan et al. ........................ 435/15 |
| 5,527,688 * | 6/1996 | Mallia ............................... 435/15 |
| 5,580,747 | 12/1996 | Shulz et al. ...................... 435/24 |
| 5,759,787 | 6/1998 | Strulovici ......................... 435/7.4 |

* cited by examiner

*Primary Examiner*—Nashaat T. Nashed
*Assistant Examiner*—Christian L. Fronda
(74) *Attorney, Agent, or Firm*—Malin, Haley & DiMaggio, P.A.

(57) ABSTRACT

The present invention is a simple, selective, rapid and a non-radioactive procedure for estimating the activity of protein kinases and protein phosphatases. The method involves attaching a suitable substrate to a 96-well plate surface and then measuring the activity of the specific enzymes using suitable incubating conditions. The PKC assay involves immobilizing histone (type III-SS), the substrate for PKC, and then determining the extent of phosphorylation by using ammonium molybdate and 1-amino-2-naphthol-4-sulfonic acid based reaction for inorganic phosphate quantitation. The PP-1 assay involves immobilizing phosphorylase-b substrate to the assay plate and then phosphorylating the substrate using phosphorylase kinase. Finally, the phosphate is hydrolyzed from the substrate by protein phosphatase. The assay methods are suitable for estimating PKC and PP-1 activity in tissue and cell samples without using any radiolabeled substrate.

8 Claims, 8 Drawing Sheets

SIMPLE NON-RADIOACTIVE ASSAY FOR ESTIMATING PROTEIN KINASE C AND PROTEIN PHOSPHATASE-1

BACKGROUND OF THE INVENTION

Protein Kinase C (PKC) is a family of serine-threonine kinases which play an important role in many cellular functions. So far, at least ten different isoforms of PKC have been identified and broadly classified into three major families named classical PKC (cPKC), novel PKC (nPKC) and atypical PKC (aPKC). Of these three families, the classical type consisting of the $\alpha$, $\beta$ (I and II), and $\gamma$ is the best characterized and most abundant. Enzymes in the cPKC family are activated by diacylglycerol in the presence of phosphatidylserine and $Ca^{++}$ subsequent to various cell activation mechanisms. However, enzymes in the nPKC family are independent of $Ca^{++}$ and the enzymes in the aPKC family are not readily activated by any of the standard second messengers such as phorbol esters and $Ca^{++}$. Since different isoforms of PKC are widely distributed in various tissues and regulate different intracellular functions, estimation of PKC activity is an important step in signal transduction research.

Normally, PKC is assayed by measuring incorporation of $^{32}P$ from ($\gamma$-$^{32}P$)ATP into suitable substrates, usually histone (type III-SS), in a reaction mixture that contains magnesium, ($\gamma$-$^{32}P$)ATP, diacylglycerol, L-$\alpha$-phosphatidyl L-serine and $Ca^{++}$. In most assays, the PKC reaction is run at 37° C. and at the end of reaction phosphorylated ($^{32}P$) substrate is removed from the rest of the reaction mixture either by using precipitation methods or by using acidic phosphocellulose papers that bind only the basic phosphorylated histone while anionic ($\gamma$-$^{32}P$)ATP may be washed away. Both of these methods involve ($\gamma$-$^{32}P$)ATP and relatively expensive radioactive measurement techniques.

A procedure has been developed in which the PKC activity is measurable using non-radiolabeled ATP and a 96-well micro-plate. Our method uses a simple substrate immobilization technique and a colorimetric analysis to determine the extent of substrate phosphorylation. The method is simple, sensitive, rapid, and specific for PKC. This method may also be used for various other protein kinases by immobilizing suitable substrates and adjusting the incubation conditions.

The second type of enzymes that can be assayed by this invention, protein phosphatases, are regulatory enzymes that antagonize the action of protein kinases within the cell. Protein phosphatases fall into two general categories: those with specificity for phosphoserine or phosphothreonine residues and those with specificity for phosphotyrosine residues. Protein tyrosine phosphatases (PTPases) play a critical role in lymphocyte signaling, cell cycling, bacterial virulence and tumorigenesis. The serine/threonine class of protein phosphatases are also involved in many aspects of cellular regulation including immunosuppression, shellfish poisoning and cell cycle control. The serine/threonine-specific protein phosphatases are divided into two groups, type-1 and type-2. The type-1 protein phosphatases (PP-1) preferentially dephosphorylate the $\beta$ subunit of phosphorylase kinase. Type-2 protein phosphatases termed PP-2A, PP-2B and PP-2C dephosphorylate the $\alpha$ subunit of phosphorylase kinase. Protein phosphatases activities are normally measured using radiolabeled substrates or by using anti-phosphotyrosine antibodies to estimate the level of dephosphorylation from the specific substrates. The above mentioned techniques involve costly equipment or hazardous radioisotopes. A need exists for a simple, non-radioactive assay for estimating protein phosphatases. The present invention is a procedure in which the PP-1 activity is measured using non-radiolabeled substrate (phosphorylase-b) and a 96-well ELISA plate reader. The method uses a simple substrate immobilization technique and a colorimetric analysis to determine the extent of dephosphorylation. The method is simple, sensitive, rapid and specific for pp-1. This method may also be used for various other protein phosphatases by immobilizing suitable substrates and adjusting the incubation conditions.

SUMMARY OF THE INVENTION

The present invention is a simple and a rapid non-radioactive procedure for estimating the activity of protein kinase C (PKC) and protein phosphatase-1 (PP-1). The PKC assay involves immobilizing histone (type III-SS), the substrate for PKC, and then determining the extent of phosphorylation by using ammonium molybdate and 1-amino-2-naphthol-4-sulfonic acid based reaction for inorganic phosphate quantitation. Histone was attached to the assay plate by incubating 200 $\mu$l of 5 mg/ml solution at 4° C. for 12 hours. After removing non-adsorbed histone from the wells the PKC mediated phosphorylation reaction was initiated by adding a reaction mixture that contained PKC enzyme preparation, phorbol 12,13-dibutyrate (PDBu), L-$\alpha$-phosphatidyl-L-serine (PS), $Ca^{++}$ and ATP (adenosine triphosphate) in 50 mM Tris HCl (pH 7.5) buffer. At the end of 15 min incubation the reaction mixture was removed and the wells were washed twice with ice cold 50 mM Tris-HCl (pH 7.5) buffer. After two washings, 200 $\mu$l of alkaline phosphatase enzyme in 1.0 M diethanolamine buffer (pH 9.8) was added to the wells to release phosphates that have been transferred from ATP to histone by PKC. At the end of alkaline phosphatase hydrolysis of phosphorylated histone, the amount of phosphates present in the incubation medium was estimated using 1-amino-2-naphthol-4-sulfonic acid. The assay method is suitable for estimating PKC activity in tissue and cell samples without using any radiolabeled ATP.

The PP-1 assay involves immobilizing phosphorylase-b substrate to the 96-well assay plate and then phosphorylating the substrate using phosphorylase kinase. The activity of PP-1 is determined by quantitating the amount of phosphates released from the substrate by using ammonium molybdate and 1-amino-2-naphthol-4-sulfonic acid based reaction for inorganic phosphate quantitation. Phosphorylase-b is attached to the assay plates by incubating 200 $\mu$l of 5.0 mg/ml solution at 4° C. for 12 hours. After removing non-adsorbed phosphorylase-b from the wells, the PP-1 mediated dephosphorylation reaction is initiated by adding a reaction mixture that contains PP-1 enzyme preparation, 1 mM EDTA, 1 mM EGTA in 50 mM Tris HCl (pH 7.5) buffer. After a 15 minute incubation at 37° C., 50 $\mu$l of the reaction mixture is transferred to wells in a new plate that contains ammonium molybdate and then the amount of phosphates released into the incubation medium is estimated using 1-amino-2-naphthol-4-sulfonic acid. The assay method is suitable for estimating PP-1 activity in tissue and cell samples without using any radiolabeled substrate.

These, and further, and other objects and features of the invention are apparent in the disclosure, which includes the above and ongoing written specification, with the drawings.

DETAILED DESCRIPTION OF THE PREFERRED EMBODIMENTS

The materials used in the protein kinase C (PKC) assay were purchased from the following sources: Histone (type III-SS), L-α-phosphatidyl L-serine, phorbol 12,13-dibutyrate (PDBu), ATP, alkaline phosphatase, Tris-hydrochloride, EDTA, calcium acetate, magnesium acetate, diethanolamine, ammonium molybdate, sodium bisulfite and 1-amino-2-naphthol-4-sulfonic acid were purchased from Sigma (St. Louis, Mo.). The 96-well plates used in this assay were purchased from Becton-Dickinson (Pro Bind, Falcon plates, No. 3915). The ELISA plate reader used was from Bio-Tek (Model: EL 307C).

Figure 1:
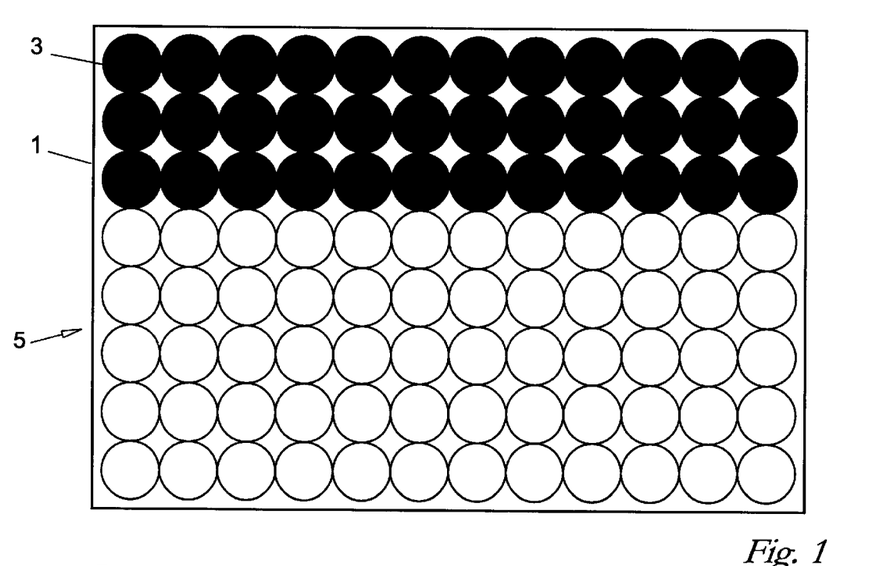
FIG. 1 shows step 1 in the protein kinase C (PKC) assay of adding histone to the wells.
Figure 2:
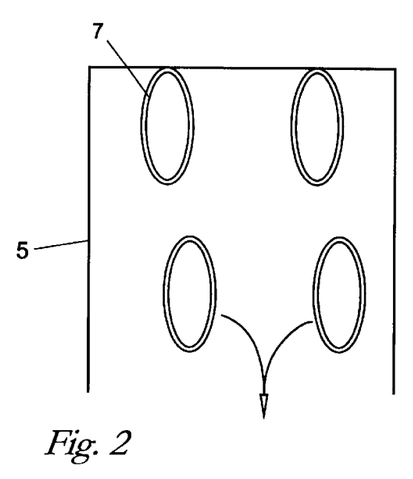
FIG. 2 shows step 2 in the PKC assay of removing excess histone by washing.

First, for the optimization of the substrate immobilization, the 96-well plate 1 is coated with histone. For this, the substrate solution was prepared by dissolving different amounts of histone, ranging from 0.5 mg/ml to 10 mg/ml in 50 mM Tris-HCl (pH 7.5) buffer. From the substrate solutions 200 µl was added to selected rows 3 of wells 5 in a 96-well plate 1, as shown in FIG. 1, and then the plate, with the substrate solutions, was allowed to stay at 4° C. for 12 hours. At the end of 12 hours of incubation, the substrate solution 7 was carefully removed from the plate and then the plate was washed with 50 mM Tris-HCl (pH 7.5) buffer twice, as shown in FIG. 2. After two washings, the substrate coated 96-well plates were kept in an inverted position on a sheet of filter paper at 4° C. for 30 minutes to remove the excess wash buffer from the wells. The amount of protein attached to each well was determined by using micro BCA (bicinchonic acid) method. The micro BCA assay revealed an increase in the substrate binding to the wells as the concentration of the substrate was increased. However, concentrations above 5 mg/ml did not produce significantly higher attachment of histone to the plates. Therefore, after initial standardization of protein binding, the plates were coated with 5.0 mg/ml histone solution for all our assays. The 5.0 mg/ml concentration was found to be optimal for our assay conditions.

Second, the following reagents and enzymes are prepared for the protein kinase C assay just before the start of the assay. Reaction buffer I consisting of 6 mM calcium acetate, 12 mole % L-α-phosphatidyl L-serine, 24 µg/ml phorbol 12,13-dibutyrate and 30 mM dithiothreitol (DTT) in 50 mM Tris-HCl buffer (pH 7.5); reaction buffer II consisting of 150 µM ATP, 45 mM magnesium acetate; and a calcium free buffer III consisting of everything as in buffer I, except that it contains 12 mM EGTA instead of 6 mM calcium acetate. For PKC enzyme preparation, the rat hippocampus, cerebellum and cortex were homogenized in a lysis buffer (20 mM Tris-HCl (pH 7.4) buffer containing 2 mM EDTA, 5 mM EGTA, 2 mM DTT, 1 mM PMSF (phenylmethylsulfonyl fluoride), 0.1% bacitracin, 0.002% each leupeptin) using a Potter Elvejhem homogenizer. The homogenate was centrifuged at 40,000×g for 40 minutes to separate the particulate and cytosolic fractions. The particulate fraction was resuspended in the lysis buffer containing 1% triton X-100, using gentle sonication on ice for 60 seconds.

Figure 3:
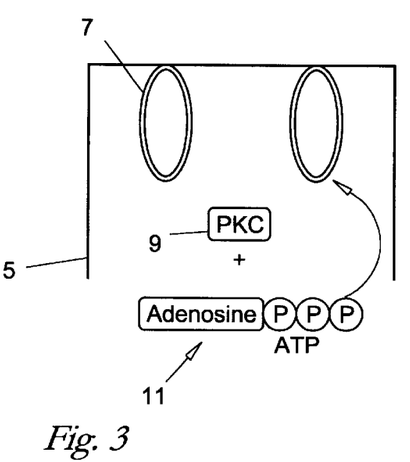
FIG. 3 shows step 3 in the PKC assay of adding the reaction buffer, the PKC enzyme preparation and Mg-ATP solution and incubating the solution.
Figure 4:
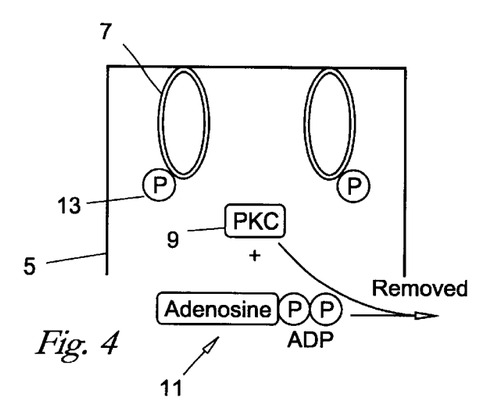
FIG. 4 shows step 4 in the PKC assay of washing the plate to remove PKC enzyme, ATP, ADP and other reactive compounds.

Then the assay of Protein Kinase C is performed. To all the wells that were used as "TEST" in the assay plate 50 µl of the reaction buffer I was added and to the "CONTROL" 50 µl of the calcium free buffer III was added. After adding the appropriate buffers, 50 µl of the enzyme preparation 9 (5 µg protein) was added to all the wells in the 96-well plate and then the plate was kept on a shaker and pre-incubated at 25° C. for 5 minutes. At the end of pre-incubation, the enzyme reaction was initiated by adding 50 µl of reaction buffer II 11 to all the wells 5 and then the plate was incubated at 25° C. for 15 minutes, as shown in FIG. 3. After 15 minutes of incubation, the reaction was terminated by emptying the contents of the plate by rapidly inverting and pouring the solutions out of the wells. Subsequently the plate was washed twice with ice cold, 50 mM Tris-HCl buffer and then the assay plate was kept in an inverted position on a filter paper for 5 minutes at 4° C.

Figure 5:
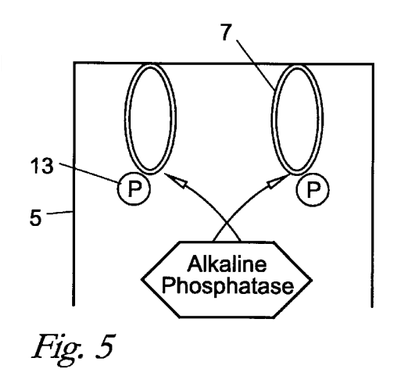
FIG. 5 shows step 5 in the PKC assay of adding alkaline phosphatase enzyme to hydrolyze the phosphates.
Figure 6:
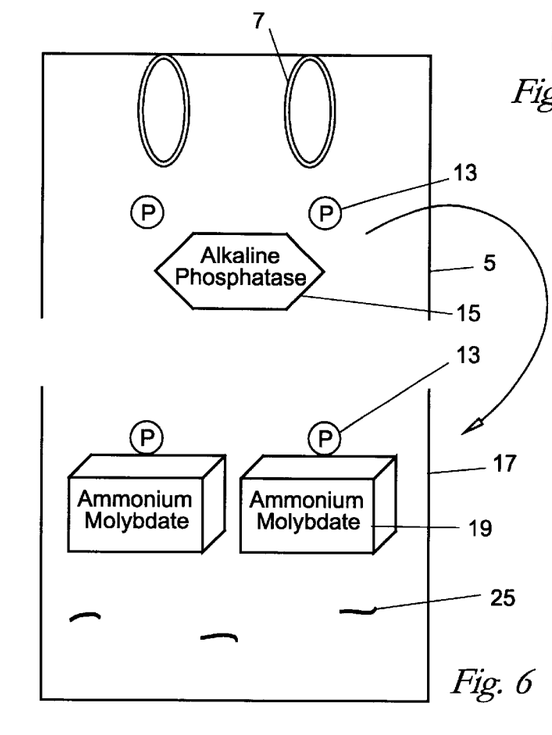
FIG. 6 shows step 6 in the PKC assay of transferring 50 µl of the solution to the wells in a new plate that contain 20 µl of ammonium molybdate.

The next step involves the releasing of phosphates 13 from histone 7 (phosphorylated substrate) using alkaline phosphatase 15, as shown in FIG. 5. In this step, 200 µl (1.0 IU) of alkaline phosphatase 15 (diluted in 1.0 M diethanolamine buffer (pH 9.8)) was added to all the wells 5 and then the plate was incubated at 37° C. for 60 minutes to ensure complete hydrolysis of phosphates 13 from the PKC phosphorylated histone 7. At the end of incubation, 50 µl of the hydrolysates from assay wells 5 were transferred immediately to correspondingly numbered wells 17 in a clean 96-well plate 27 (FIG. 8B) that contained 20 µl of ammonium molybdate 19, as shown in FIG. 6.

Figures 7, 8A:
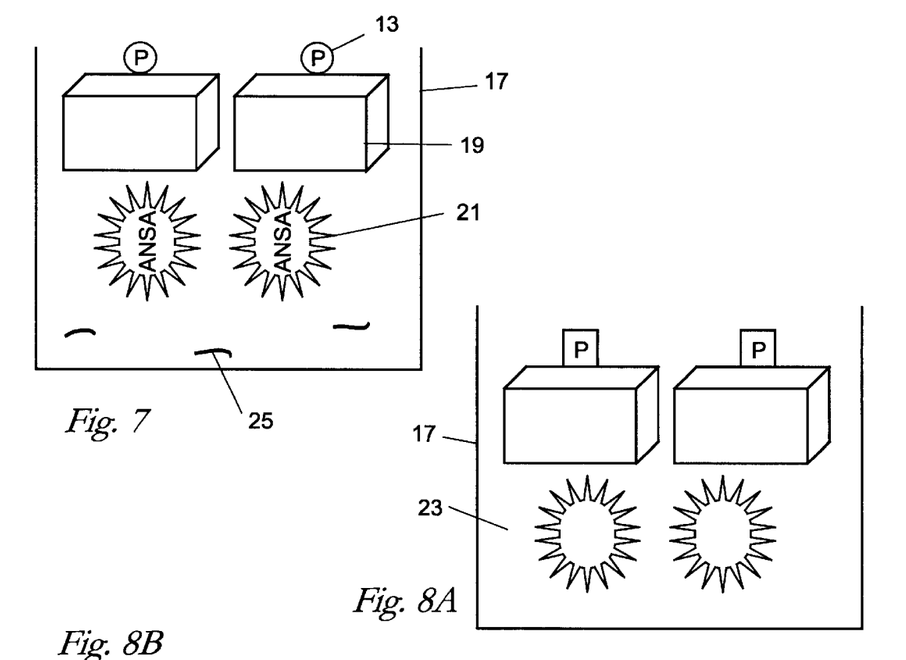
FIG. 7 shows step 7 in the PKC assay of adding 8 µl of 1-amino-2-naphthol-4-sulfonic acid (ANSA) to the wells, shaking for five minutes and then incubating for twenty minutes at 37° C.
FIGS. 8A and 8B show a well and a 96-well plate in which wells with a higher level of PKC activity show an intense blue color that is directly proportional to the concentration of phosphate released from histone.
Figure 8B:
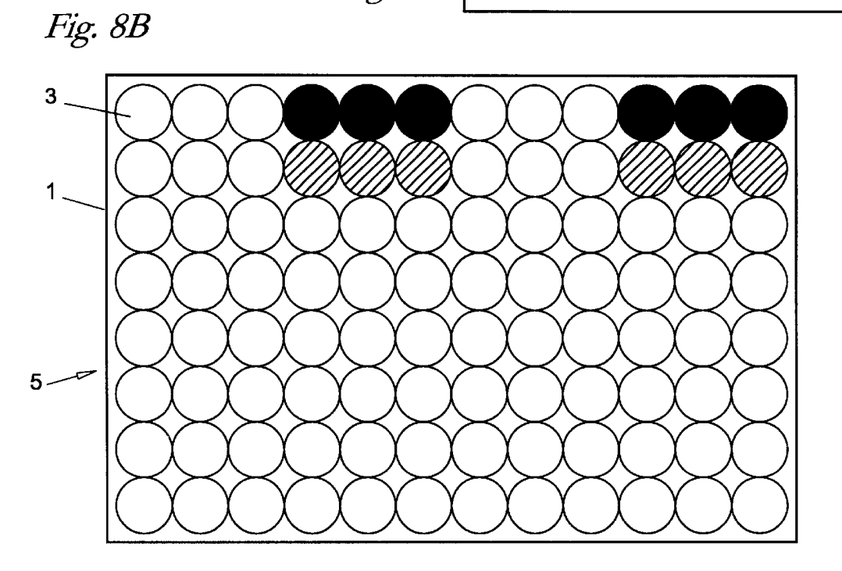

Next, the amount of phosphate 13 present in the wells 17 was estimated. The final phosphate estimation in our assay was achieved using ammonium molybdate 19 and 1-amino-2-nathol-4-sulfonic acid 21. In this step, when ammonium molybdate 19 is added to a solution containing free phosphates 13, ammonium phosphomolybdic acid is formed which is reduced by the addition of 1-amino-2-naphthol-4-sulfonic acid reagent 21 to heteropolymolybdenum that produces a blue color 23 in solution, as shown in FIGS. 8A and 8B. The intensity of this colored complex can be measured at 620 nm, which is proportional to the amount of phosphates present in the wells and therefore estimating the exact amount of phosphates released from histone was possible.

In the final step of our assay, 50 µl of the alkaline phosphatase hydrolysate was added to the wells containing 20 µl of ammonium molybdate solution (prepared by dissolving 2.5 g of ammonium molybdate in 20 ml of de-ionized water and mixed with 30 ml of 10 N sulfuric acid. The acid ammonium molybdate solution was finally diluted to 100 ml with de-ionized water). The addition of hydrolysate was followed by 8 µl of 1-amino-2-naphthol-4-sulfonic acid (prepared by mixing 0.5 g of 1-amino-2-naphthol-4-sulfonic acid in 195 ml of 15% sodium bisulfite solution followed by the addition of 5 ml of 20% sodium sulfite 25 to ensure complete dissolution of 1-amino-2-naphthol-4-sulfonic acid. The solution was stored at 4° C. in a brown bottle until use) and 100 µl of de-ionized water to each well. The plate was put on a shaker for 5 minutes and then it was transferred to a 37° C. incubator for 20 minutes. A set of phosphate standards (1 µg to 10 µg) prepared by dissolving necessary amount of monosodium phosphate that gave the phosphate concentration of 100 µg/ml was treated similarly to obtain the calibration curve. The total amount of phosphates present in each assay well was calculated which represented the amount of phosphates released from phosphorylated histone by alkaline phosphatase. The total amount of phosphates present in each well, in turn, is equal to the amount γ phosphate transferred from ATP to histone by PKC. After determining the amount of phosphates that were released from histone, the PKC enzyme activity was calculated as follows:

$$\mu \text{ moles of phosphate transferred } (P) \text{ per minute} = \frac{\mu \text{ moles of phosphate present in well}}{PKC \text{ enzyme incubation time}}$$

Figure 9:
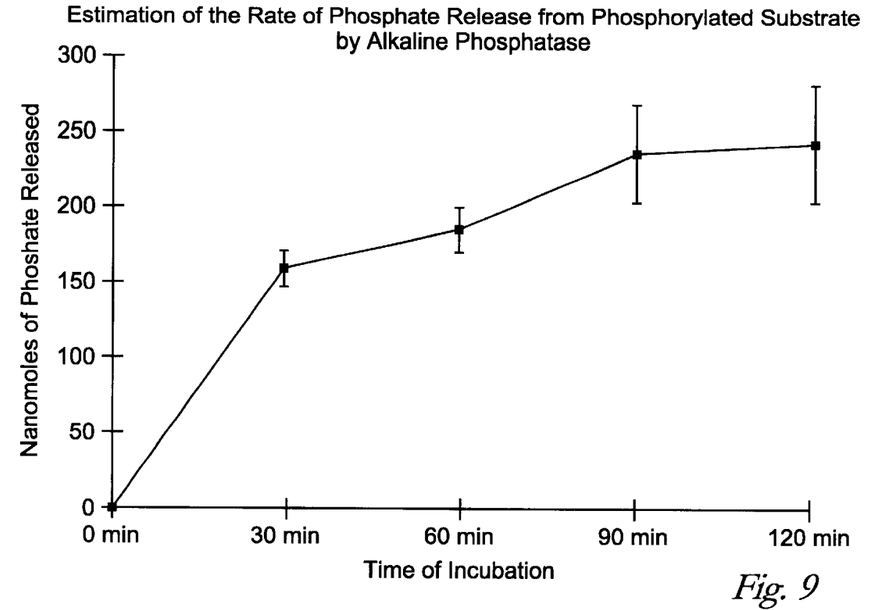
FIG. 9 is a graph of the estimation of the rate of phosphate released from the phosphorylated substrate by alkaline phosphatase for a given incubation time.
Figure 10:
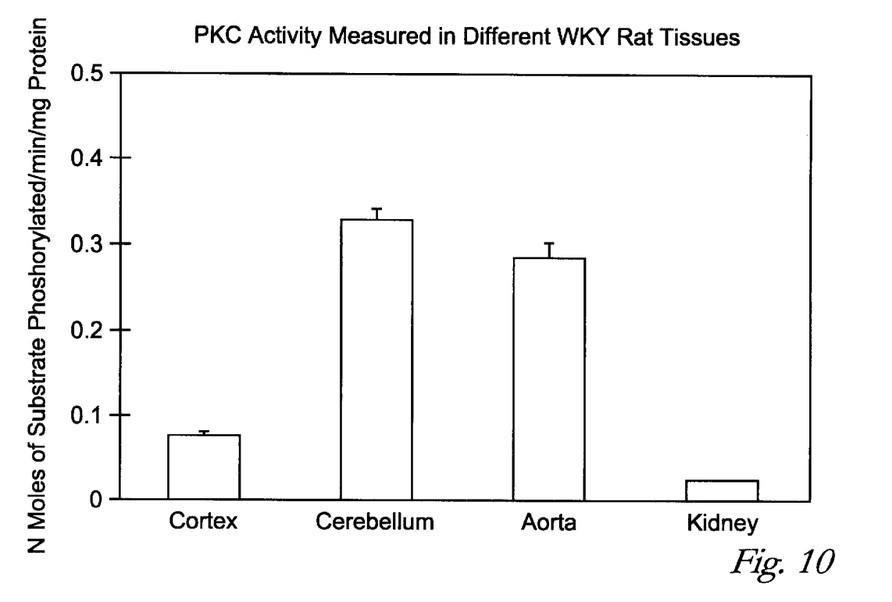
FIG. 10 is a graph of PKC activity measured in various rat tissues.
Figure 11:
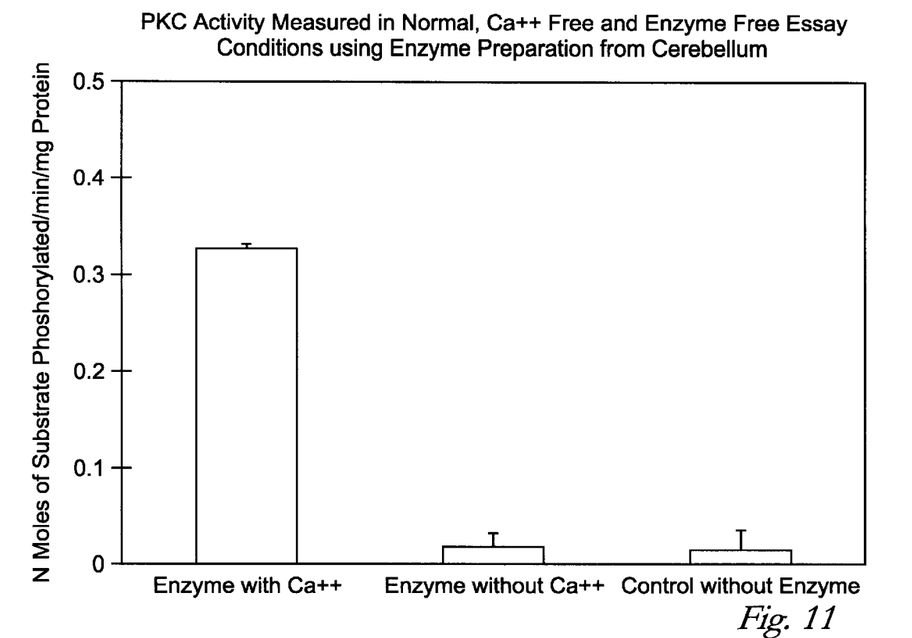
FIG. 11 is a graph of PKC activity measured in normal $Ca^{++}$ free conditions and also the activity in enzyme free control.

To validate the assay, the PKC activity in different regions of the rat brain was measured, as shown in FIG. 10. The new assay was able to measure the activity of the PKC in cortex, hippocampus and cerebellum of the rat brain. To determine the specificity of the assay for PKC two types of controls were used, one without the enzyme preparation and the second control with $Ca^{++}$ free incubation buffer, as shown in FIG. 11. In both controls, phosphorylation of the substrate was absent, however absence of enzyme activity in $Ca^{++}$ free buffer confirmed that the enzyme activity measure in this assay was that of $Ca^{++}$ dependent PKC. Also, in the inventive PKC assay the amount of enzyme used and the length of incubation are found to be two critical factors, as shown in FIG. 9, since excess of these two may easily saturate the immobilized substrate with phosphorylation. Therefore, it is recommended that for comparing the activity of PKC in two different samples or to determine the true levels of PKC activity it is necessary not to phosphorylate the entire amount of substrates that have been immobilized. In the assay, 5 µg total of the PKC enzyme preparations were used and the incubating time was kept at 15 minutes or lower.

In the dephosphorylation step, with alkaline phosphatase, we used a 60 minute incubation time to release the phosphates from PKC phosphorylated histone. Since a 60 minute incubation was able to release all the phosphates from histone, stopping alkaline phosphatase enzyme reaction was not critical. At the end of alkaline phosphatase reaction, 50 µl aliquots of the hydrolysates were transferred to corresponding wells in a new 96-well plate that contained 20 µl of the ammonium molybdate solution. The assay was completed by adding 8 µl of 1-amino-2-naphthol-4-sulfonic acid. The final measurement of the color intensity was done using a ELISA plate reader. Though we used an ELISA plate reader in our experiments, the final measurement may also be achieved by using either a spectrophotometer or a colorimeter that may be adjustable to measure the color intensity at 620 nm. The assay is simple and is usable for measuring the activity of other protein kinase by immobilizing suitable substrates and adjusting the incubation conditions.

The materials used in the protein phosphatase-1 (PP-1) assay were purchased from the following sources: Phosphorylase-b, phosphorylase kinase, ATP, alkaline phosphatase, Tris-hydrochloride, EDTA, calcium acetate, magnesium acetate, diethanolamine, ammonium molybdate, sodium bisulfite and 1-amino-2-naphthol-4-sulfonic acid were purchased from Sigma (St. Louis, Mo.). The 96-well plates used in this assay were purchased from Becton-Dickinson (Pro Bind, Falcon plates No. 3915,). The ELISA plate reader used was from Bio-Tek (Model: EL 307C).

Figure 12:
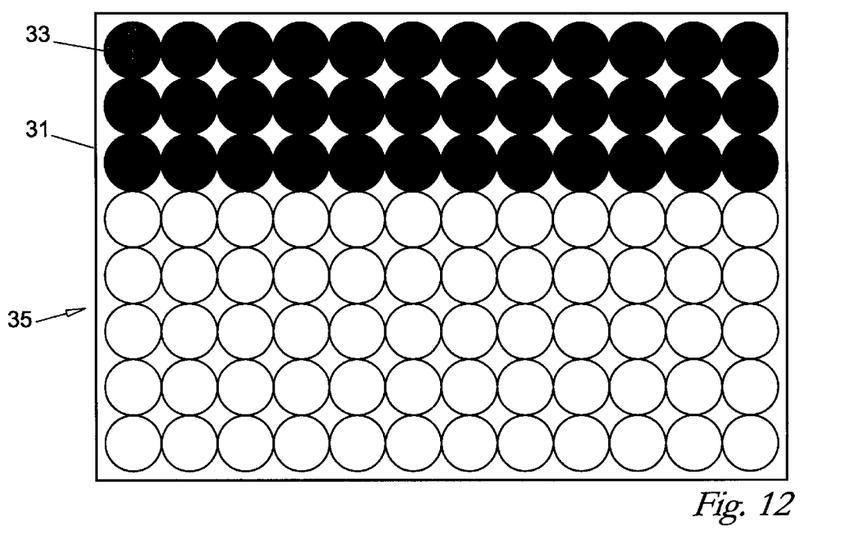
FIG. 12 shows step 1 in the protein phosphatase-1 (PP-1) assay of adding the substrate phosphorylase-b to the wells.
Figures 13, 14, 15, 16:
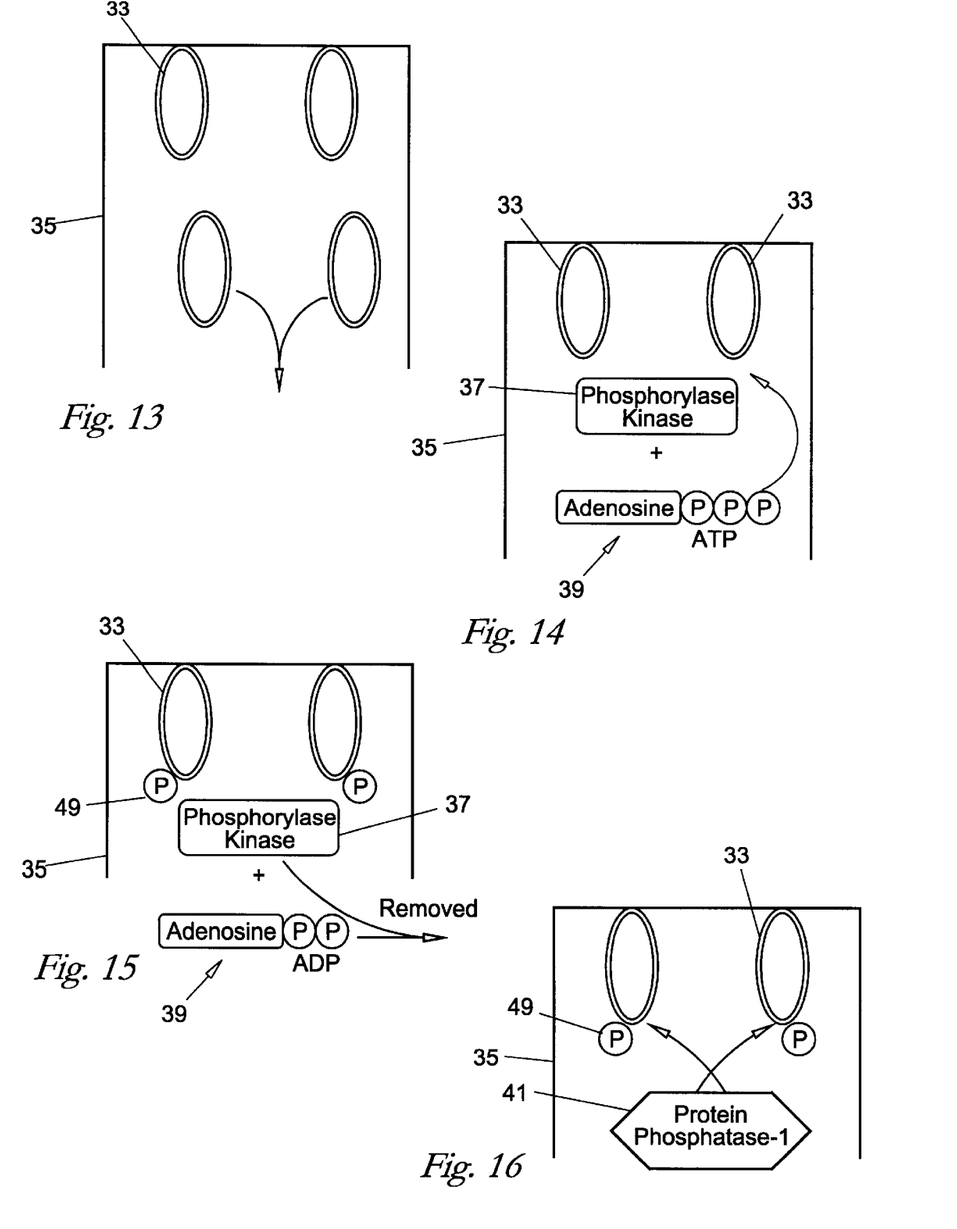
FIG. 13 shows step 2 in the PP-1 assay of removing excess phosphorylase-b from the wells by washing.
FIG. 14 shows step 3 in the PP-1 assay of adding phosphorylase kinase to the wells and then incubating the well plate.
FIG. 15 shows step 4 in the PP-1 assay of washing the plate to remove phosphorylase kinase enzyme, ATP and other reactive compounds.
FIG. 16 shows step 5 in the PP-1 assay of adding protein phosphatase-1 enzyme preparation to hydrolyze the phosphates from the substrate.

The first step involves coating the 96-well plate 31 with phosphorylase-b 33. Initially, the substrate solution was prepared by dissolving different amounts of phosphorylase-b, ranging from 0.5 mg/ml to 10 mg/ml in 50 mM Tris-HCl (pH 7.5) buffer. From the substrate solutions, 200 µl was added to a set of wells 35 in a 96-well plate and then the plate was allowed to stay at 4° C. for 12 hours, as shown in FIG. 12. At the end of the 12 hour incubation period, the substrate solution 33 was removed from the plate and then the plate was washed carefully with 50 mM Tris-HCl (pH 7.5) buffer twice, as shown in FIG. 13. After two washings, the substrate coated 96-well plates 31 were kept in an inverted position on a sheet of filter paper at 4° C. for 30 minutes to remove the excess wash buffer from the wells 35. The amount of protein attached to each well was determined by using micro BCA (bicinchonic acid) method. The micro BCA assay revealed an increase in the substrate binding to the wells as the concentration of the substrate was increased. However, concentrations above 5 mg/ml did not produce significantly higher attachment of phosphorylase-b to the plates. Therefore, after initial standardization of protein binding, the plates were coated with 5 mg/ml phosphorylase-b solution for all our assays, since this concentration was found to be optimal for our assay conditions.

Next, the substrate was phosphorylated with Phosphorylase kinase 37, as shown in FIG. 14. Phosphorylase kinase solution was prepared by dissolving 1 mg of crystallized enzyme preparation (200–500 units) in 5 ml of 50 mM Tris-HCl buffer 39 (pH 7.6) containing 0.1% β-mercaptoethanol, 2 mM ATP and 15 mM caffeine. 200 µl of the enzyme solution was added to each well 35 and then the assay plate was incubated at 37° C. for two (2) hours to ensure complete phosphorylation of all the immobilized substrate. At the end of incubation, the enzyme solution was carefully removed and the plate was washed three times with ice cold Tris-HCl buffer (pH 7.6) to remove the enzyme 37 and ATP 39 from the plate, as shown in FIG. 15. After three (3) washings, the plate was kept on a sheet of filter paper in an inverted position at 4° C. for 30 minutes to remove the excess buffer from the plate. The dry plate was then used for PP-1 activity measurement.

Figures 17, 18, 19A:
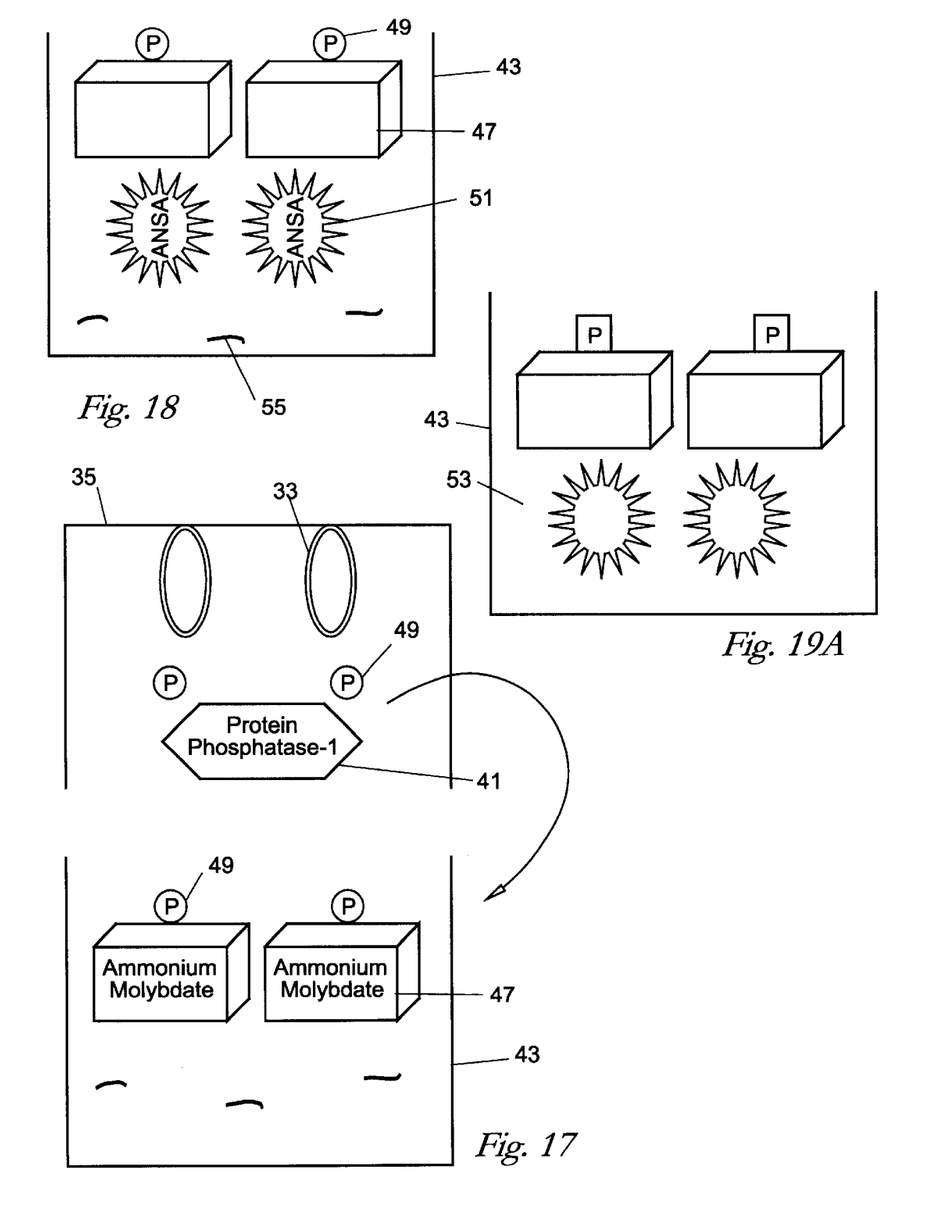
FIG. 17 shows step 6 in the PP-1 assay of transferring the solution to wells in a new plate that contain ammonium molybdate.
FIG. 18 shows step 7 in the PP-1 assay of adding 1-amino-2-naphthol-4-sulfonic acid to the well, shaking the solution and then incubating the plate.
FIGS. 19A and 19B show a well and a 96-well plate in which wells that received a higher level of PP-1 showed an intense blue color that is directly proportional to the concentration of phosphate released from phosphorylase-b.

In the next step, the protein Phosphatase-1 (PP-1) activity was measured. For measuring PP-1 activity, the untreated PC12 cells were lysed by sonication in 20 mM imidazole-HCl (pH 7.2) buffer containing 0.1 mM EDTA, 0.1% β-mercaptoethanol, 0.1% BSA, 1 mM PMSF (phenylmethylsulfonylfluoride), 0.1% bacitracin, 0.002% each leupeptin and aprotinin. To all the wells 35 in the plate 31 that are used for the assay, 150 µl of the 20 mM imidazole buffer (pH 7.2) containing 0.1 mM EDTA, 0.1% BSA and 0.1% β-mercaptoethanol was added. The plate was pre-incubated at 37° C. for 15 minutes to warm-up the buffer and then 50 µl of the enzyme preparation 41 (0.5 µg) was added to appropriate wells, as shown in FIG. 16. Enzyme blanks were setup as controls which received 50 µl of lysis buffer instead of enzyme solution. The plates were incubated at 37° C. again for 15 minutes. At the end of incubation, 50 µl of the reaction mixture was transferred immediately to the corresponding wells 43 in a new 96-well plate 45 (FIG. 19B) that contained 20 µl of ammonium molybdate solution 47, as shown in FIG. 17.

Figure 19B:
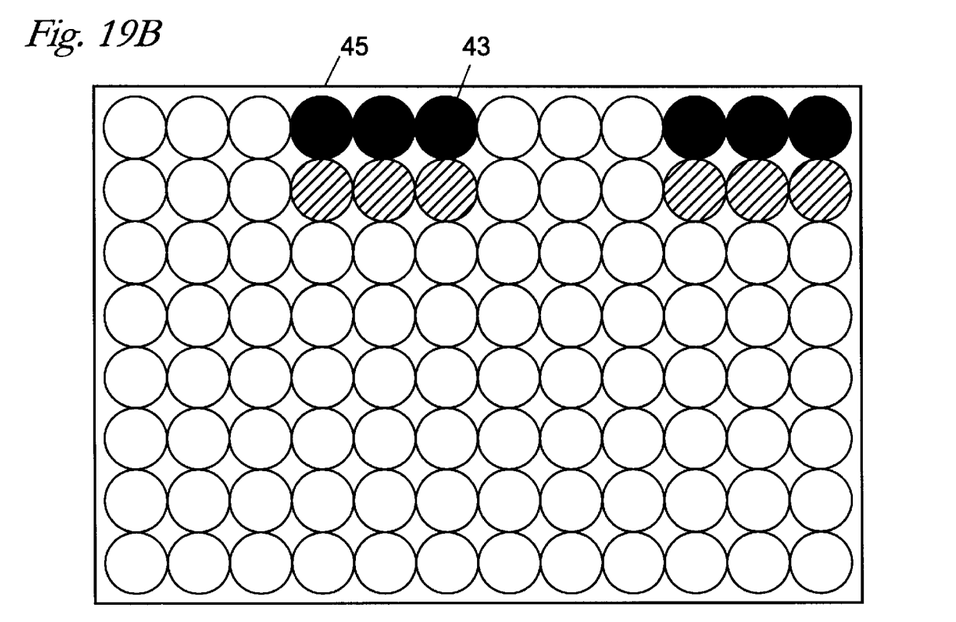

Next, the amount of phosphate 49 present in the wells 43 was estimated. The final phosphate estimation in the assay was achieved using ammonium molybdate 47 and 1-amino-2-nathol-4-sulfonic acid 51, as shown in FIG. 18. In this step, when ammonium molybdate is added to a solution containing free phosphates, ammonium phosphomolybdic acid is formed which is reduced by the addition of 1-amino-2-naphthol-4-sulfonic acid reagent to heteropolymolybdenum that produces a blue color 53 in solution, as shown in FIGS. 19A and 19B. The intensity of this colored complex can be measured at 620 nm, which is proportional to the amount of phosphates present in the wells and therefore estimating the amount of phosphates 49 released from phosphorylase-b 33 is possible.

In the final step of our assay, to the wells containing 20 µl of ammonium molybdate solution 47 (prepared by dissolving 2.5 g of ammonium molybdate in 20 ml of de-ionized water and mixed with 30 ml of 10 N sulfuric acid. The acid ammonium molybdate solution was finally diluted to 100 µl with de-ionized water) 50 µl of the protein phosphatase-1 hydrolysate was added. The addition of hydrolysate was followed by 8 µl of 1-amino-2-naphthol-4-sulfonic acid 51 (prepared by mixing 0.5 g of 1-amino-2-naphthol-4-sulfonic acid in 195 ml of 15% sodium bisulfite solution followed by the addition of 5 ml of 20% sodium sulfite to ensure complete dissolution of 1-amino-2-naphthol-4-sulfonic acid. The solution was stored at 4° C. in a brown bottle until use) and 100 µl of de-ionized water 55 to each well. The plate was put on a shaker for five (5) minutes and then it was transferred to 37° C. incubator for twenty (20) minutes. A set of phosphate standards (1 µg to 10 µg) prepared by dissolving necessary amount of monosodium phosphate that gave the phosphate concentration of 100 µg/ml was treated similarly to obtain the calibration curve. The total amount of phosphate present in each well represented the amount of phosphate released from phosphorylated substrate by protein phosphatase-1. After determining the amount of phosphate 49 that was released from phosphorylase-b 33, the PP-1 enzyme activity was calculated as follows:

$$\mu \text{ moles of phosphate released } (P) \text{ per minute} = \frac{\mu \text{ moles of phosphate present in well}}{\text{PP-1 enzyme incubation time}}$$

Figure 20:
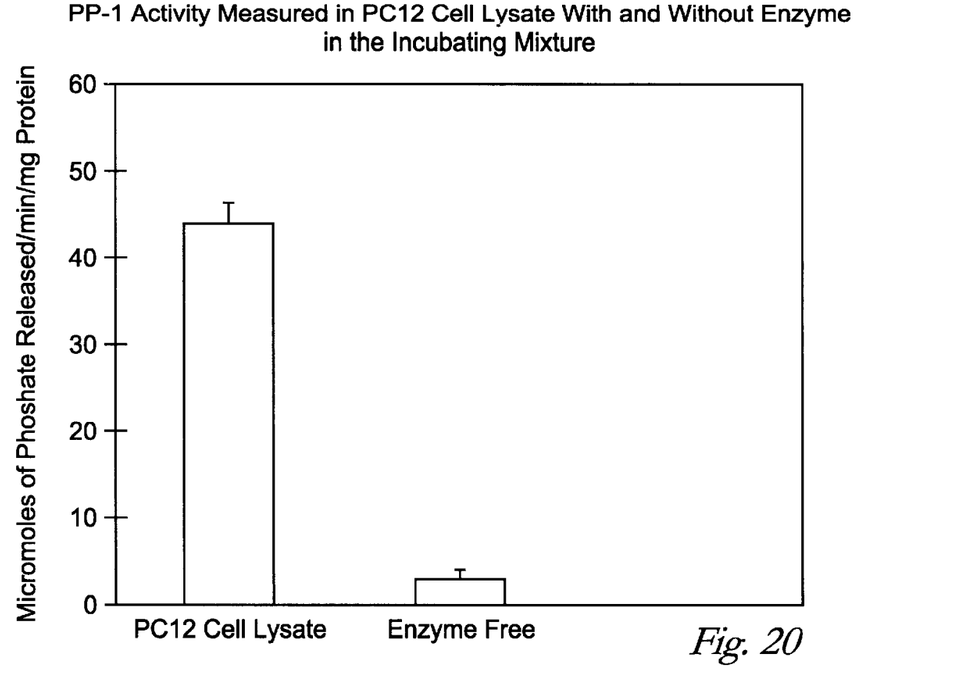
FIG. 20 is a graph of PP-1 activity measured in PC12 cell lystate with and without an enzyme in the incubating mixture.

The protein phosphatase-1 assay method was able to estimate the activity of PP-1 in the PC 12 cell lysates used in the experiments, as shown in FIG. 20. During PP-1 enzyme incubation, maximum care was taken to adjust the enzyme concentration, since high concentrations dephosphorylate the substrate very rapidly. Also, the length of incubation was not allowed to exceed 15 minutes. At the end of incubation, 50 µl aliquots were rapidly transferred to wells that contained ammonium molybdate and the phosphate estimation was completed. Since the amount of enzyme preparation used was very dilute, no precipitation of proteins was seen after mixing with ammonium molybdate and 1-amino-2-naphthol-4-sulfonic acid.

The PP-1 assay is relatively fast and simple. It involves a simple calorimetric method for estimating phosphate and therefore does not involve any radioactive substrates. The first step in the assay is unique since phosphorylase-b, the substrate for PP-1 enzyme, is phosphorylated in the plate itself after immobilization by phosphorylase kinase. Once the assay plates were prepared by immobilizing a suitable substrate and phosphorylating them with necessary kinase, the rest of the assay was completed in less than two hours. A similar approach may be used for estimating the activity of other phosphatases also by immobilizing suitable substrates. The new assay is not only rapid it also enables us to screen a large number of samples and therefore is a very efficient technique.

While the invention has been described with reference to specific embodiments, modifications and variations of the invention may be constructed without departing from the scope of the invention.

We claim:

1. A non-radioactive assay method for estimating the activity of protein kinase C (PKC) comprising providing a first well plate, attaching a peptide or protein substrate to the first well plate, washing the first well plate with a buffer to remove unattached substrate, adding a first reaction buffer to the first well plate, adding a PKC enzyme preparation to the first well plate, placing the first well plate on a shaker and preincubating, adding a second reaction buffer comprising a phosphoryl donor nucleotide to the first well plate to phosphorylate the substrate, incubating the first well plate, washing the first well plate with a buffer to remove everything except the phosphorylated substrate from the first well plate, adding an alkaline phosphatase to the first well plate to release phosphates from the phosphorylated substrate, incubating the first well plate to ensure hydrolysis of phosphates from the phosphorylated substrate to create hydrolysates, providing a second well plate, adding a first solution to the second well plate, transferring the hydrolysates from the first well plate to the second well plate to create a second solution, providing an instrument to measure color intensity, determining the amount of phosphates present in the second solution in the second well plate by measuring the color intensity of the second solution with the instrument, and determining the activity of protein kinase C from the amount of phosphates present in the second well plate.

2. The method of claim 1, wherein the attaching a substrate to the first well plate comprises attaching a histone substrate.

3. The method of claim 1, wherein the attaching a substrate to the first well plate comprises incubating the first well plate to attach the substrate to the first well plate.

4. The method of claim 1, wherein the washing with a buffer comprises washing with Tris-HCl.

5. The method of claim 1, wherein the adding a first reaction buffer to the first well plate comprises adding a solution comprising calcium acetate, L-α-phosphatidyl L-serine, phorbol 12,13-dibutyrate and dithiothreitol in a Tris-HCl buffer.

6. The method of claim 1, wherein the adding a second reaction buffer to the first well plate comprises adding adenosine triphosphate and magnesium acetate.

7. The method of claim 1, wherein the adding a first solution to the second well plate comprises adding ammonium molybdate and 1-amino-2-naphthol-4-sulfonic acid.

8. The method of claim 1, wherein the providing an instrument to determine color intensity comprises providing an instrument selected from a group consisting of an ELISA plate reader, a spectrophotometer, and a calorimeter.

* * * * *